(12) United States Patent
Yin (10) Patent No.: US 12,313,528 B2
(45) Date of Patent: May 27, 2025

(54) CUVETTE FOR ANALYSIS OF LIQUIDS

(71) Applicant: COBIO SMART HEALTHCARE TECHNOLOGY CO., LTD., Shanghai (CN)

(72) Inventor: Yu Yin, Shanghai (CN)

(73) Assignee: Cobio Smart Healthcare Technology Co., Ltd., Shanghai (CN)

( * ) Notice: Subject to any disclaimer, the term of this patent is extended or adjusted under 35 U.S.C. 154(b) by 232 days.

(21) Appl. No.: 17/886,146

(22) Filed: Aug. 11, 2022

(65) Prior Publication Data

US 2023/0041914 A1 Feb. 9, 2023

Related U.S. Application Data

(63) Continuation-in-part of application No. PCT/CN2020/075244, filed on Feb. 14, 2020.

(51) Int. Cl.
| | |
|---|---|
| *G01N 21/03* | (2006.01) |
| *G01N 21/11* | (2006.01) |
| *G01N 21/05* | (2006.01) |
| *G01N 21/27* | (2006.01) |

(52) U.S. Cl.
CPC .......... *G01N 21/03* (2013.01); *G01N 21/11* (2013.01); *G01N 2021/0382* (2013.01); *G01N 2021/054* (2013.01); *G01N 21/274* (2013.01)

(58) Field of Classification Search
CPC ........ G01N 21/03; G01N 21/05; G01N 21/11; G01N 21/274; G01N 2021/0382; G01N 2021/054; G01N 21/07
See application file for complete search history.

(56) References Cited

U.S. PATENT DOCUMENTS

| | | | | |
|---|---|---|---|---|
| 3,751,173 | A * | 8/1973 | Sanz | G01N 21/05 356/246 |
| 4,823,168 | A * | 4/1989 | Kamahori | G01N 21/05 250/576 |
| 2006/0233667 | A1 | 10/2006 | Samsoondar | |
| 2010/0203621 | A1 † | 8/2010 | Takahashi | |

(Continued)

FOREIGN PATENT DOCUMENTS

| | | |
|---|---|---|
| CN | 200790000098.4 U | 10/2007 |
| CN | 201380075 Y | 1/2010 |

(Continued)

OTHER PUBLICATIONS

International Search Report and Written Opinion for PCT/CN2020/075244, dated Nov. 19, 2020.

*Primary Examiner* — Abdullahi Nur
(74) *Attorney, Agent, or Firm* — Andrus Intellectual Property Law, LLP (57) ABSTRACT

A cuvette for analysis of liquids, including a first cuvette portion and a second cuvette portion, which are joined together, with a cuvette cavity, an inlet passage and an outlet passage being formed between the first cuvette portion and the second cuvette portion, the inlet passage and the outlet passage both in communication with the cuvette cavity, wherein the outlet passage is provided therein with a labyrinth-like sealing structure, which prevents backfill of a gas that has been discharged from the outlet passage during filling of a liquid to be analyzed in the cuvette.

20 Claims, 4 Drawing Sheets

(56) References Cited

U.S. PATENT DOCUMENTS

| | | | |
|---|---|---|---|
| 2015/0198521 A1* | 7/2015 | Moldt | G01N 21/05 |
| | | | 356/246 |
| 2018/0050339 A1 | 2/2018 | Pouteau et al. | |
| 2019/0009286 A1 | 1/2019 | Collinson et al. | |

FOREIGN PATENT DOCUMENTS

| | | | |
|---|---|---|---|
| CN | 103852576 | A | 6/2014 |
| CN | 201420437092.5 | U | 8/2014 |
| CN | 204107521 | U | 1/2015 |
| CN | 204973940 | U | 1/2016 |
| CN | 105327722 | A | 2/2016 |
| CN | 108136418 | A | 6/2018 |
| CN | 209656563 | † | 11/2019 |
| CN | 209656563 | U | 11/2019 |
| CN | 209706895 | U | 11/2019 |
| CN | 209780139 | U | 12/2019 |
| EP | 1256027 | B1 | 1/2008 |
| WO | 2016139409 | A1 | 9/2016 |
| WO | 2021159457 | † | 8/2021 |

\* cited by examiner
† cited by third party

CUVETTE FOR ANALYSIS OF LIQUIDS

FIELD OF THE INVENTION

The present application relates to the field of liquid analysis technology and, in particular, to a cuvette for analysis of liquids.

DESCRIPTION OF THE PRIOR ART

In the fields of life sciences, medicine and healthcare, food, environmental protection, etc., it is often necessary to analyze liquids, in particular compositions of liquids. There are various methods available for liquid analysis, which typically involve analysis, isolation and detection of liquid samples, for example, isolation of protein peptides in the field of life sciences, analysis of beverage compositions in the field of food, research on drug ingredients in the field of pharmaceuticals, analysis of body fluids such as urine, plasma and serum in the field of medicine and healthcare, and so forth.

Optical detection is a common liquid analysis means for observing a liquid with an optical instrument such as a microscope to obtain information about compositional components therein, which is in particular suitable for analysis of body fluids in the field of medicine and healthcare. For optical analysis of liquids such as urine, there are many conventional cuvette designs, which typically utilizing shallow cuvettes or test tubes. They are transparent to probing light, or their analysis cavities for containing liquids to be analyzed and parts for transmission therethrough of probing light is transparent to the probing light. Such a cuvette for liquid analysis is usually made up of two interconnected parts, one on top of the other. Such a cuvette also includes an inlet for filling the liquid to be analyzed, an outlet for discharging air bubbles and an excess of the liquid, and the analysis cavity for containing the liquid to be analyzed.

A Chinese utility model patent (Application No. 200790000098.4) provides a cuvette for centrifugal isolation in a filled state and then optical analysis of liquids, as a disposable product. This cuvette is composed of joined upper and lower portions and includes an analysis space for accommodating a liquid to be analyzed, an inlet port for filling the liquid to be analyzed, an inlet passage connected between the inlet port and the analysis space, an outlet port for discharging bubbles and an excess of the liquid, and a buffer channel connected between the outlet port and the analysis space. As a cuvette for urine analysis, it can work with an automated urine sediment analyzer to achieve automated analysis of urine sediments in a urine specimen. The buffer channel in the cuvette is designed as a meandering serpentine shape. This is a large-volume design allowing the liquid to be injected at a high rate from the inlet port with a pipette, without the problem of overflow of the liquid due to sudden topping-up upon its entry into the buffer channel. In order to ensure that the liquid following toward corners of the cuvette will not be discharged from the inlet and outlet ports during a centrifugal operation, the inlet and outlet ports are disposed away from the corners of the cuvette in a middle cuvette region between two adjacent ones of the corners. However, during practical use, it has been found that when the injected liquid fills a predetermined length of the buffer channel, e.g., ⅔ of its total length, bubbles will be introduced into the analysis space when the cuvette is subject to a centrifugal operation, making normal detection impossible. It would appropriate that the injected liquid reaches the outlet port (or a location with a distance of not greater than 1 mm from an edge at the outlet port). However, this will inevitably lead to overflow of the liquid during a centrifugal operation. Since the inlet and outlet ports are arranged in a middle cuvette region between two adjacent corners of the cuvette, they are very close to each other, the liquid that has overflowed from one or both of them during a centrifugal operation will pool around both of them. When a curved pipette (with a ~2 mm long pipette tip) is used to draw off the overflow liquid, the pipette tip of the curved pipette will be inevitably held closer to one of the two ports, and therefore a greater suction force will be applied to the port and a channel connected thereto, possibly causing partial removal of the liquid from the port and the channel connected thereto in an attempt to completely draw off the overflow liquid and hence a flow of the liquid from the analysis space toward the channel, which may affect the detection results.

A Chinese utility model patent (Application No. 201420437092.5) discloses a cuvette for analysis of liquids, which includes a first cuvette portion and a second cuvette portion, which are joined with each other. The first cuvette portion is provided thereon with a first recess, a first through hole and a second through hole, and the second cuvette portion is provided thereon with a second recess. A space between the first recess and the second recess defines an analysis cavity, an inlet passage and an outlet passage, which are in communication with one another. A passage port from the inlet passage to the analysis cavity and a passage port from the outlet passage to the analysis cavity are disposed respectively on opposite sides of a line connecting the first through hole and a center of the analysis cavity. The inlet passage includes a flared first passage section. In this patent, the structure of the analysis cavity is inconducive to rapid wetting of a liquid and is prone to each generation of void bubbles during wetting. Moreover, gas backfill tends to occur in a gas discharge passage during sedimentation of a liquid being analyzed, and a calibration mark for focusing and positioning is not easily recognizable optically and unfavorable to automated production.

SUMMARY OF THE INVENTION

In view of the above described shortcomings of the prior art, it is an object of the present application to provide a cuvette for analysis of liquids, which enables faster wetting of a liquid within the cuvette while avoiding the generation of bubbles and gas backfill. It is designed with a calibration mark for easier optical recognition and automated production.

In order to achieve the above object, the present application provides a cuvette for analysis of liquids, comprising:
  a first cuvette portion and a second cuvette portion, which are joined to each other, the first cuvette portion having a first recess, a first through hole and a second through hole, the first through hole located out of the first recess, the second cuvette portion having a second recess, the first recess open toward the second cuvette portion, the second recess open toward the first cuvette portion, the first recess and the second recess confining a space therebetween forming a cuvette cavity, an inlet passage and an outlet passage, which are in communication with one another, the first through hole in communication with the inlet passage, the second through hole in communication with the outlet passage,
  a first passage port from the inlet passage to the cuvette cavity and a second passage port from the cuvette cavity to the outlet passage disposed respectively on opposite sides of a line connecting the first through hole to a center of the cuvette cavity, the inlet passage comprising a flared first passage section, wherein the cuvette cavity is provided therein with an elongate groove; and the outlet passage is provided therein with at least two baffle blocks, which project from inner walls of the outlet passage along radially directions of the outlet passage, block parts of radial cross-sections of the outlet passage, and are arranged in a staggered manner to form a labyrinth-like sealing structure.

Further, the elongate groove is an arc-shaped groove provided in a bottom surface of the second recess and extending along a lengthwise direction of a side wall of the cuvette cavity. The elongate groove has a cross-section, which is arc-shaped and tangent to a side wall of the second recess.

Further, the elongate groove is located between the first passage port and the second passage port.

Further, the number of the at least two baffle blocks is two, and they are respectively a first baffle block and a second baffle block.

Further, the first baffle block projects from a bottom surface of the first recess toward the inside of the outlet passage, and the second baffle block projects from the bottom surface of the second recess toward the inside of the outlet passage.

Further, the first baffle block is closer to the second passage port than the second baffle block.

Further, the cuvette cavity has four corners, and the first passage port and the second passage port are adjacent to two of the corners of the cuvette cavity that are proximate the first through hole.

Further, two of the corners of the cuvette cavity away from the first through hole are rounded corners, and side wall portions of the cuvette cavity at the rounded corners are arc-shaped.

Further, the arc-shaped side wall portions of the cuvette cavity have radii of curvature that are not less than 2 mm.

Further, the inlet passage has a curved third passage section. An opening of the third passage section at one end thereof forms the first passage port, a side wall portion of the third passage section away from the center of the cuvette cavity is arc-shaped.

Further, the arc-shaped side wall portion of the third passage section has a radius of curvature that is not less than 2 mm.

Further, the inlet passage further includes a second passage section between the third passage section and the first passage section. The first passage section is flared from the first through hole toward the second passage section, and the second passage section is a passage section with a constant width.

Further, the outlet passage includes a curved fourth passage section and a straight fifth passage section. The fourth passage section is smoothly joined to the fifth passage section.

Further, an opening of the second through hole at a first end thereof is brought into communication with the fifth passage section at one end thereof.

Further, the outlet passage has a U-like shape with one arm in communication with the fifth passage section and another arm with an opening on one side thereof, which forms the second passage port.

Further, the first cuvette portion is provided in its external surface with a third recess, and the second cuvette portion is provided in its external surface with a fourth recess. The third recess and the fourth recess have bottom surfaces, which are both flat, smooth and parallel to joining surfaces of the first cuvette portion and the second cuvette portion. A portion of the first cuvette portion between a bottom surface of the third recess and a bottom surface of the first recess forms a first viewing window for the cuvette cavity, and a portion of the second cuvette portion between a bottom surface of the fourth recess and a bottom surface of the second recess forms a second viewing window for the cuvette cavity.

Further, the first cuvette portion and the second cuvette portion are injection-molded.

Further, the first through hole resembles a funnel and has a first opening in communication with the inlet passage and a second opening provided on a surface of the first cuvette portion. A width of the first through hole gradually increases from the first opening toward the second opening.

Further, the cuvette also includes a calibration mark disposed within the cuvette cavity on a bottom surface of the second cuvette portion.

Further, the calibration mark is a photolithographic pattern formed by a photolithographic process.

In order to achieve the above object, the present application provides a cuvette for analysis of liquids, comprising:

a first cuvette portion and a second cuvette portion, which are joined together, with a cuvette cavity, an inlet passage and an outlet passage being formed between the first cuvette portion and the second cuvette portion, the inlet passage and the outlet passage both in communication with the cuvette cavity, wherein the outlet passage is provided therein with a labyrinth-like sealing structure, which prevents backfill of a gas that has been discharged from the outlet passage during filling of a liquid to be analyzed in the cuvette.

Further, the labyrinth-like sealing structure comprises at least two baffle blocks, each of which projects inwardly from an inner wall of the outlet passage and blocks part of a path within the outlet passage, and which are arranged in a sequentially staggered manner.

Further, the at least two baffle blocks include a first baffle block and a second baffle block, which project inwardly from the inner walls of the outlet passage respectively in two opposite directions.

Further, the cuvette cavity is provided therein with an elongate groove, which facilitates wetting of the liquid and is located at a bottom of the cuvette cavity and is adjacent to a side wall of the cuvette cavity.

Further, the elongate groove is so formed as to be recessed from the bottom of the cuvette cavity and has a cross-section which is arc-shaped and tangent to the side wall that it is adjacent to.

Further, the inlet passage is provided with a first passage port in communication with the cuvette cavity at one end and with a first through hole in communication with the outside of the cuvette at the other end, and the outlet passage is provided with a second passage port in communication with the cuvette cavity at one end and with a second through hole in communication with the outside of the cuvette at the other end.

Further, the outlet passage has a U-like shape with one arm in communication with the cuvette cavity and another arm in communication with the second through hole.

Further, the first passage port and the second passage port are located respectively on opposite sides of a line connecting the first through hole and a center of the cuvette cavity.

Further, the inlet passage comprises a first passage section, which provides the first passage port at one end and has an inner diameter varying so as to be greater at a location of the first passage section closer to the first passage port.

Further, the inlet passage further comprises a second passage section in communication with the first passage section and a third passage section in communication with the second passage section, the second passage section being straight and having a constant width, the third passage section curved and in communication with the second through hole at one end.

Further, the first through hole resembles a funnel having a first opening formed at its larger end and a second opening formed at its smaller end, the first opening in communication with the outside of the cuvette, the second opening in communication with the inlet passage.

Further, the cuvette further comprises a calibration mark disposed within the cuvette cavity on a bottom surface of the second cuvette portion.

Further, the calibration mark is a photolithographic pattern formed by a photolithographic process.

Further, the first cuvette portion is provided thereon with a first recess and the second cuvette portion is provided thereon with a second recess, the first recess open toward the second cuvette portion, the second recess open toward the first cuvette portion, the first recess and the second recess confining a space therebetween, which forms the cuvette cavity, the inlet passage and the outlet passage. The first through hole and the second through hole are both provided on the first cuvette portion.

Further, the first cuvette portion is provided in an external surface thereof with a third recess and the second cuvette portion is provided in an external surface thereof with a fourth recess, the third recess and the fourth recess having bottom surfaces, which are both flat, smooth and parallel to joining surfaces of the first cuvette portion and the second cuvette portion. A portion of the first cuvette portion between a bottom surface of the third recess and a bottom surface of the first recess forms a first viewing window for the cuvette cavity, and a portion of the second cuvette portion between a bottom surface of the fourth recess and a bottom surface of the second recess forms a second viewing window for the cuvette cavity.

Further, wherein, the cuvette cavity is a rectangular parallelepiped having two corners away from the outlet passage and the inlet passage, which are rounded.

Further, the first cuvette portion and the second cuvette portion are injection-molded.

In order to achieve the above object, the present application provides a cuvette for analysis of liquids, comprising:
  a first cuvette portion and a second cuvette portion, which are joined to each other, the first cuvette portion having a first recess, a first through hole and a second through hole, the second cuvette portion having a second recess, the first recess recessed in a direction from an internal surface of the first cuvette portion to an external surface thereof, the first recess open toward the second cuvette portion, the second recess recessed in a direction from an internal surface of the second cuvette portion to an external surface thereof, the second recess open toward the first cuvette portion, the first recess and the second recess confining a space therebetween forming a cuvette cavity, an inlet passage and an outlet passage, which are in communication with one another, the first through hole extending through the first cuvette portion in a thickness direction of the first cuvette portion and coming into communication with the inlet passage, the second through hole extending through the first cuvette portion in the thickness direction of the first cuvette portion and coming into communication with the outlet passage,
  a first passage port from the inlet passage to the cuvette cavity and a second passage port from the cuvette cavity to the outlet passage disposed respectively on opposite sides of a line connecting the first through hole to a center of the cuvette cavity,
  wherein a backflow edge of the cuvette cavity is provided thereat with an elongate groove, which is a groove disposed in a bottom surface of the second recess and extends along a lengthwise direction of a side wall of the cuvette cavity, the elongate groove having a cross-section, which is arc-shaped and tangent to a side wall of the second recess; and
  the outlet passage is provided therein with a first baffle block and a second baffle block, which project inwardly from inner walls of the outlet passage respectively in two opposite directions and block part of a path within the outlet passage, thereby forming a labyrinth-like sealing structure.

Further, the cuvette further comprises a calibration mark, which is disposed within the cuvette cavity on a bottom surface of the second cuvette portion and is a photolithographic pattern formed by a photolithographic process.

Further, the first cuvette portion and the second cuvette portion are both injection-molded and are joined together by welding.

The cuvettes for analysis of liquids of the present application have the following beneficial technical effects:
1. A liquid in need of analysis is injected into the cuvette cavity from the inlet passage. In this process, under the action of surface tension, the liquid gradually wets a peripheral circumference of the cuvette cavity. In order to achieve a good wetting effect, a relatively slow sample injection rate would be desirable. Through providing the groove (channel) at the backflow edge of the cuvette cavity, faster wetting of the liquid within the cuvette cavity can be achieved while ensuring a good wetting effect, enabling an increased sample feed rate.
2. After the liquid enters the cuvette cavity, gas backfill tends to occur in the course of accelerated sedimentation. Through arranging the at least two baffle sheets of the labyrinth-like sealing structure in the outlet passage, gas backfill can be prevented, ensuring accuracy of the analysis.
3. The use of a photolithographic pattern as the calibration mark is conducive to optical identification and allows accurate size control during fabrication, making it suitable for mass production.

DETAILED DESCRIPTION OF THE PREFERRED EMBODIMENTS

Below, the accompanying drawings of this specification are referenced to introduce many preferred embodiments of the present application so that the techniques thereof become more apparent and readily understood. This application may be embodied in many different forms of embodiment, and the protection scope of the application is not limited only to the embodiments mentioned herein.

Throughout the accompanying drawings, structurally identical parts are indicated with identical reference numerals, and structurally or functionally similar components are indicated with similar reference numerals. The size and thickness of each component in the drawings are arbitrarily depicted, and the present application is not limited to any size or thickness of each component. For greater clarity of illustration, the thicknesses of some parts are exaggerated as appropriate somewhere in the drawings.

Figure 1:
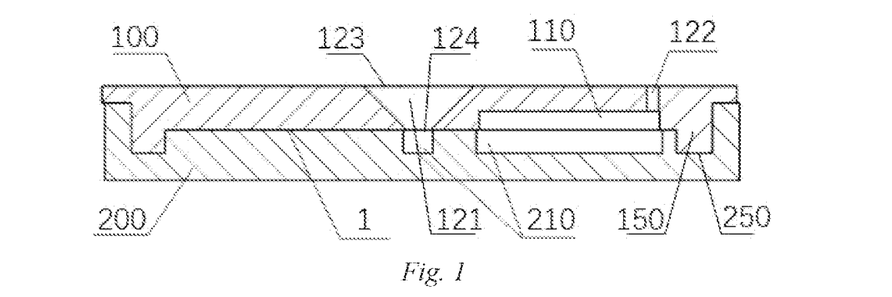
FIG. 1 is a schematic cutaway view of a cuvette for analysis of liquids according to the present application.

As shown in FIG. 1, in a preferred embodiment of the present application, there is provided a cuvette for analysis of liquids composed of a first cuvette portion 100 and a second cuvette portion 200, which are joined to each other. In this embodiment, in order to work with an automated urine sediment analyzer, it is made as a rectangular parallelepiped with square faces. It has substantially equal length and width, as well as a small thickness. For example, both the length and width are 19 mm, and the thickness is 2.81 mm. It is to be noted that, in other embodiments, this cuvette for analysis of liquids may also have another shape, such as cylindrical.

The first cuvette portion 100 and the second cuvette portion 200 are transparent to probing light. In this embodiment, they are injection-molded and transparent to the probing light (which is visible light). The two are joined together by ultrasonic welding into one integral piece. In other embodiments of the present invention, in order to adapt to different detection environments and detection accuracy requirements, the first cuvette portion 100 and the second cuvette portion 200 may be made of other materials and joined to together into one piece using other fabrication processes.

The first cuvette portion 100 has a first recess 110, and the second cuvette portion 200 has a second recess 210. When the first cuvette portion 100 and the second cuvette portion 200 are joined together, the first recess 110 and the second recess 210 defines a cuvette cavity 300, an inlet passage 330 and an outlet passage 340, which are in communication with one another. During use, a liquid in need of analysis is injected from the inlet passage 330, and in the course of the liquid entering the cuvette cavity 300, under the action of surface tension, the liquid gradually wets a peripheral circumference of the cuvette cavity 300. In order to achieve a good wetting effect, a relatively slow sample injection rate would be desirable. In order to allow a faster sample injection rate, a channel 226 is provided at a backflow edge of the second cuvette portion 200, which is inconducive to the wetting of the liquid. The channel 226 is an elongate groove, which can facilitate faster wetting of the liquid, resulting in an effective increase in the sample feed rate. The outlet passage 340 is used for discharging of a gas and an excess of the liquid. During the sample injection process, with the liquid increasingly filling the cuvette cavity 300, the gas is discharged from the outlet passage 340. During accelerated sedimentation of the liquid, a gas may be filled back in the cuvette cavity 300. In order to avoid this from happening, a labyrinth-like sealing structure 341 (see FIG. 8) is provided within the outlet passage to prevent gas backfill. The labyrinth-like sealing structure 341 refers to a number of obstacles which are arranged within the outlet passage to divide a fluid path therein into multiple tortuous path sections overall resembling a labyrinth. For example, at least two baffle sheets are provided in the outlet passage 340. These baffle sheets project within the outlet passage 340 to block part of the path in the outlet passage 340 without completely occluding the outlet passage 34. The multiple baffle sheets are sequentially staggered in such a manner that one baffle sheet projects inwardly from an inner wall of the outlet passage, and an adjacent baffle sheet projects inwardly from the inner wall of the outlet passage in the opposite direction, and so forth, thus forming the labyrinth-like structure that can prevent gas backfill. It is to be understood that the labyrinth-like sealing structure 341 is limited to as being implemented in the way according to the present embodiment, and any other structure capable of forming a tortuous path is applicable to the present application. The structure of the cuvette for analysis of liquids according to this embodiment will be described in detail below.

Figure 2:
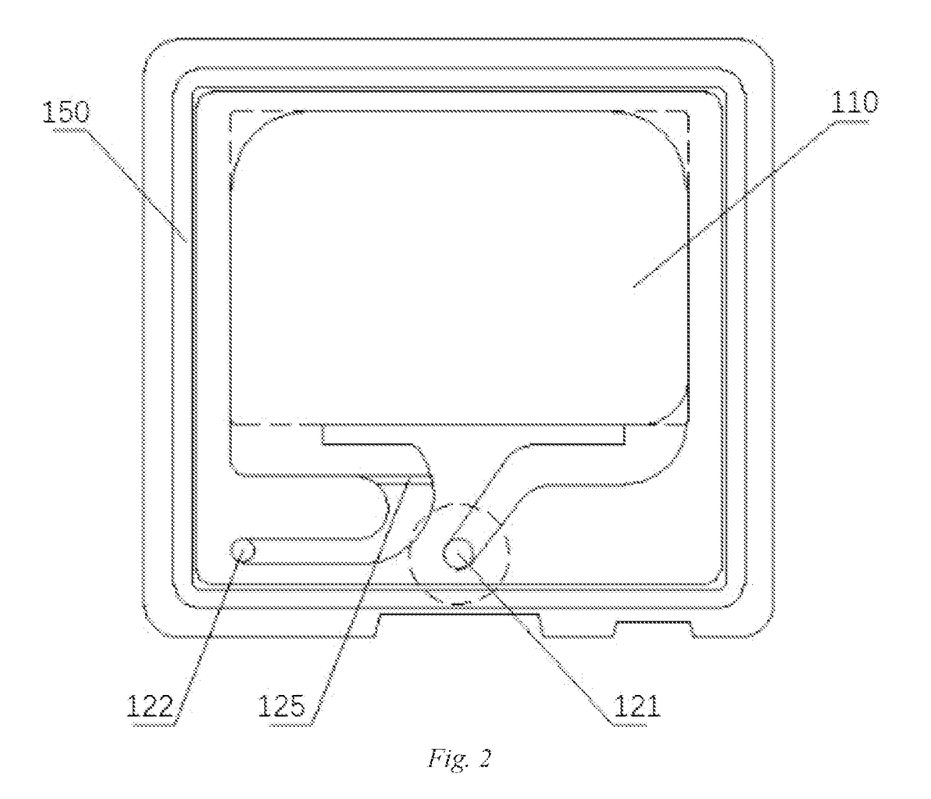
FIG. 2 is a schematic diagram illustrating an internal surface of a first cuvette portion of the cuvette for analysis of liquids shown in FIG. 1.
Figure 7:
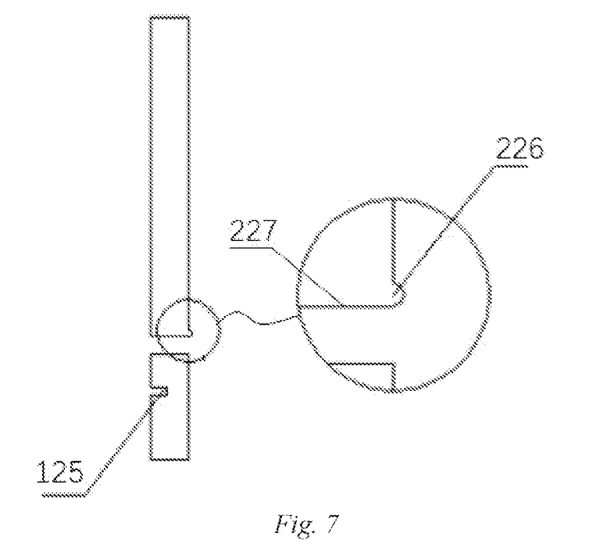
FIG. 7 of a schematic cross-sectional view along E-E in FIG. 6.
Figure 8:
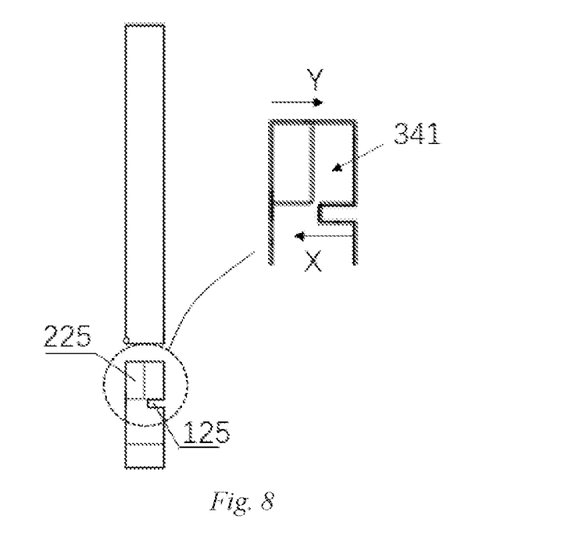
FIG. 8 of a schematic cross-sectional view along F-F in FIG. 6.

As shown in FIG. 1, the first cuvette portion 100 includes the first recess 110, a first through hole 121, a second through hole 122, a third recess 140 and a first flange 150. In this embodiment, the first cuvette portion 100 is also a rectangular parallelepiped with square faces. Preferably, its thickness is half that of the cuvette. FIG. 2 shows the shape and appearance of an internal surface of the first cuvette portion 100. This internal surface is a surface of the first cuvette portion 100 where it is joined to the second cuvette portion 200. As can be seen, the first cuvette portion 100 has the first recess 110 and openings of the first through hole 121 and the second through hole 122 on the internal surface. The opening of the first through hole 121 is out of the first recess 110, while the opening of the second through hole 122 is within the first recess 110. The first recess 110 is recessed from the internal surface of the first cuvette portion 100 along a normal of the internal surface toward the other surface (external surface). Preferably, the first recess 110 has an inner wall parallel to the normal of the internal surface and a flat and smooth bottom surface parallel to the internal surface. The first flange 150 is an annulus running around the internal surface of the first cuvette portion 100 and raised from the internal surface of the first cuvette portion 100. A portion of the first recess 110 for forming the outlet passage 340 is provided with a first baffle sheet 125, which protrudes from the bottom of the first recess 110 and extends toward the second cuvette portion 200 (in a first direction X, as shown in FIG. 8) a length that does not lead to complete closure of the outlet passage 340. That is, there is a gap left between the top of the first baffle sheet 125 facing toward the second cuvette portion 200 and the bottom of the second recess 210 (as shown in FIG. 7).

Figure 3:
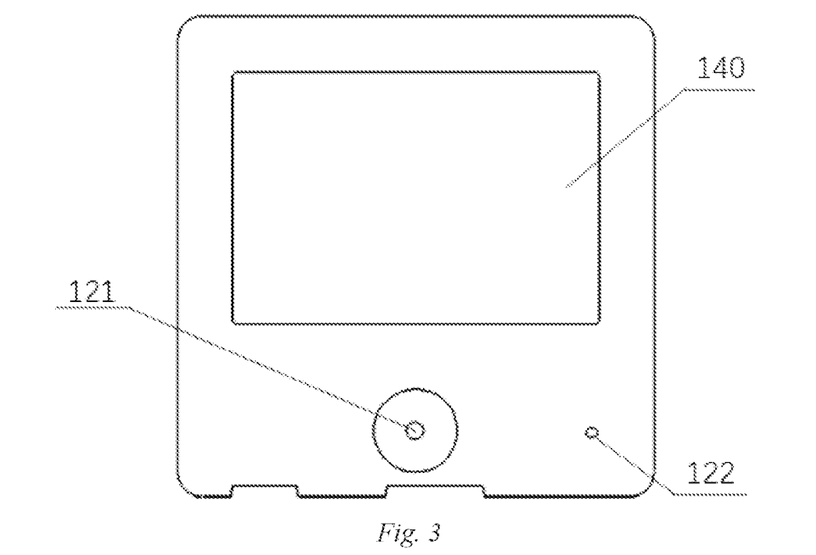
FIG. 3 is a schematic diagram illustrating an external surface of the first cuvette portion shown in FIG. 2.

FIG. 3 shows the shape and appearance of the external surface of the first cuvette portion 100. The external surface is an upper surface of the cuvette. As can be seen, the first cuvette portion 100 has the third recess 140 and openings of the first through hole 121 and the second through hole 122 on the external surface. The openings of the first through hole 121 and the second through hole 122 are both out of the third recess 140. The third recess 140 is recessed from the external surface of the first cuvette portion 100 along a normal of the external surface toward the other surface (internal surface). Preferably, it has an inner wall parallel to the normal of the external surface and a flat and smooth bottom surface parallel to the external surface (and also to the internal surface of the first cuvette portion 100).

Figure 4:
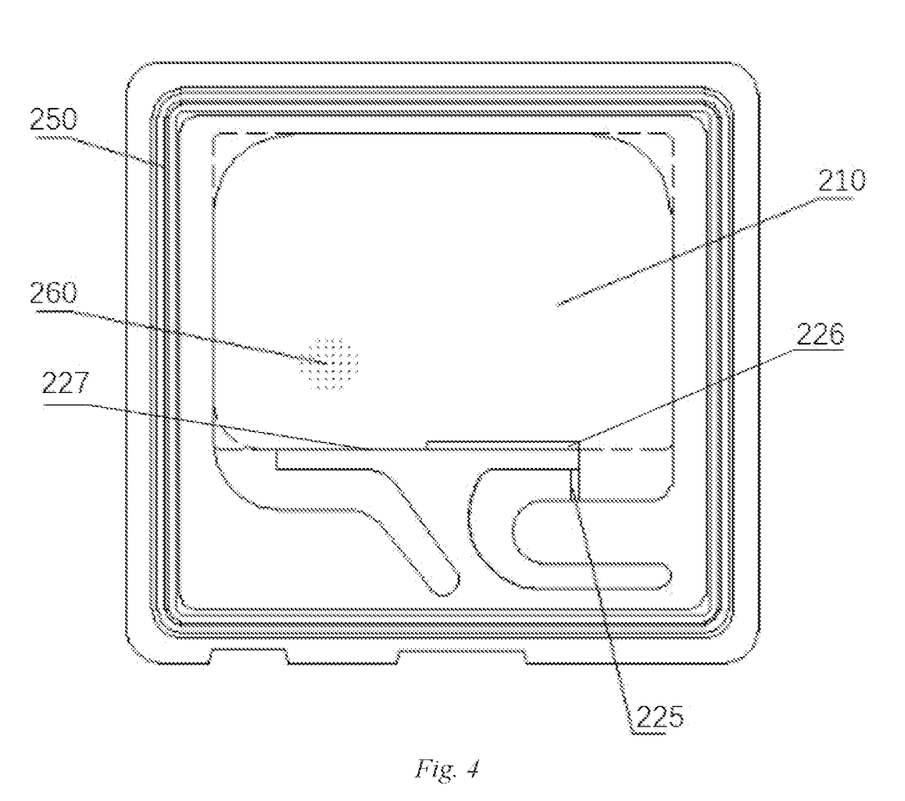
FIG. 4 is a schematic diagram illustrating an internal surface of a second cuvette portion of the cuvette for analysis of liquids shown in FIG. 1.
Figure 5:
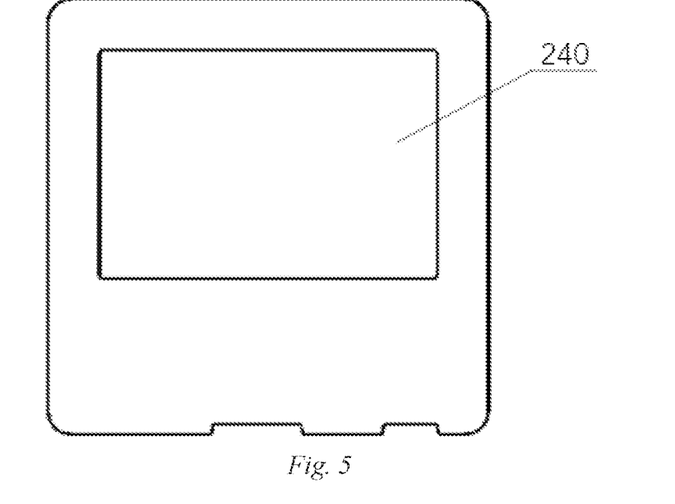
FIG. 5 is a schematic diagram illustrating an external surface of the second cuvette portion shown in FIG. 4.

As shown in FIGS. 1, 4 and 5, the second cuvette portion 200 includes a second recess 210, a fourth recess 240 and an annular groove 250. In this embodiment, the second cuvette portion 200 is also a rectangular parallelepiped with square faces. Preferably, its thickness is half that of the entire cuvette. FIG. 4 shows the shape and appearance of an internal surface of the second cuvette portion 200. The internal surface is a surface of the second cuvette portion 200 where it is joined to the first cuvette portion 100. As can be seen, the second cuvette portion 200 has the second recess 210 on the internal surface. The second recess 210 is recessed from the internal surface of the second cuvette portion 200 along a normal of the internal surface toward the other surface (external surface). Preferably, the second recess 210 has an inner wall parallel to the normal of the internal surface and a flat and smooth bottom surface parallel to the internal surface. The annular groove 250 is a groove running around the internal surface of the second cuvette portion 200 and recessed from the internal surface of the second cuvette portion 200 toward the external surface thereof. The annular groove 250 matches the first flange 150. In a portion of the second recess 210 for forming the cuvette cavity 300, an intersection of a side wall 227 of the second recess 210 between a first passage port 310 and a second passage port 320 and the bottom surface of the second recess 210 forms the backflow edge that is inconducive to wetting of a liquid, and the channel (elongate groove) 226 is provided there. The channel 226 has a cross-section (as shown in FIG. 7) that is arc-shaped and tangent to the side wall 227. A portion of the second recess 210 for forming the outlet passage 340 is provided with a second baffle sheet 225, which protrudes from the bottom of the second recess 210 and extends toward the first cuvette portion 100 (in a second direction Y, which opposite to the first direction X, as shown in FIG. 8), a length that does not lead to complete closure of the outlet passage 340. That is, there is a gap left between the top of the second baffle sheet 225 facing toward the first cuvette portion 200 and the bottom of the first recess 110. Moreover, the second baffle sheet 225 is located at a different location from the first baffle sheet 125 in the outlet passage 340. The second baffle sheet 225 may be closer to the second passage port 320 than the first baffle sheet 125 (as shown in FIG. 8).

FIG. 5 shows the shape and appearance of the external surface of the second cuvette portion 200. The external surface is a lower surface of the cuvette. As can be seen, the second cuvette portion 200 has the fourth recess 240 on the external surface. The fourth recess 240 is recessed from the external surface of the second cuvette portion 200 along a normal of the external surface toward the other surface (internal surface). Preferably, it has an inner wall parallel to the normal of the external surface and a flat and smooth bottom surface parallel to the external surface (and also to the aforesaid internal surface).

Figure 6:
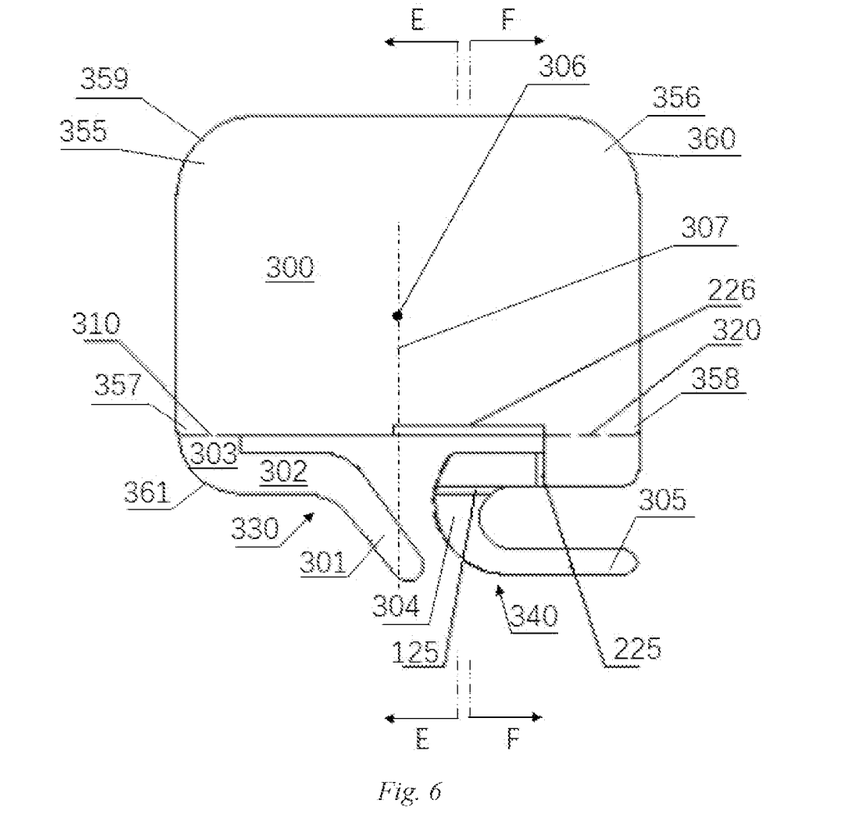
FIG. 6 is a schematic diagram illustrating the structures of a cuvette cavity, an inlet passage and an outlet passage.

FIG. 6 shows the cuvette cavity 300, the inlet passage 330 and the outlet passage 340 in the present embodiment. As can be seen, in this embodiment, the cuvette cavity 300 has a rectangular cross-section parallel to the joining surfaces 1, which has four corners: a first corner 355, a second corner 356, a third corner 357 and a fourth corner 358, in which the first corner 355 and the second corner 356 are rounded. Preferably, an arc-shaped side wall 359 at the first corner 355 has a radius of curvature that is not less than 2 mm, and an arc-shaped side wall 360 at the second corner 356 has a radius of curvature that is not less than 2 mm. A portion of the cuvette cavity 300 (upper portion) is provided on the first cuvette portion 100, and the rest thereof (lower portion) is provided on the second cuvette portion 200. A top surface of the cuvette cavity 300 is provided by part of the bottom surface of the first recess 110, and a bottom surface of the cuvette cavity 300 is provided by part of the bottom surface of the second recess 210. The cuvette cavity 300 has four side walls, which are formed by side wall portions of the first recess 110 and side wall portions of the second recess 210, which are joined together. Preferably, the four side walls of the cuvette cavity 300 are parallel to respective four side walls of the cuvette.

In some embodiments, the inlet passage 330 is provided only on the second cuvette portion 200 and has a top surface provided by part of the internal surface of the first cuvette portion 100, a bottom surface provided by part of the bottom surface of the second recess 210 and side walls formed by side wall portions of the second recess 210 and the internal surface of the first cuvette portion 100, which are joined together. In some other embodiments, as shown in FIGS. 2 and 4, a portion of the inlet passage 330 is provided on the first cuvette portion 100, and the rest thereof is provided on the second cuvette portion 200, wherein its top surface is provided by part of the bottom surface of the first recess 110 and its bottom surface is provided by part of the bottom surface of the second recess 210. The inlet passage 330 has, joined sequentially, a third passage section 301, a second passage section 302 and a first passage section 303. The third passage section 301 is connected at one end thereof to the first through hole 121. An opening of the first passage section 303 at one end thereof serves as the first passage port 310 from the inlet passage 330 to the cuvette cavity 300. The third passage section 301 is a flared passage section. In particular, it has a width gradually increasing from the first through hole 121 to the second passage section 302. The second passage section 302 is a straight passage section with a constant width, which are joined smoothly at opposite ends respectively with the third passage section 301 and the first passage section 303. The first passage section 303 is a curved passage section having an arc-shaped side wall portion away from a center 306 of the cuvette cavity 300. This arc-shaped side wall portion 361 is contiguous with and tangent to one side wall of the cuvette cavity 300. Preferably, the arc-shaped side wall portion has a radius of curvature that is not less than 2 mm. In this embodiment, the center 306 of the cuvette cavity 300 refers to its geometric center, or a center of gravity of a liquid when the cuvette cavity 300 is filled up by the liquid.

A portion of the outlet passage 340 (upper portion) is provided on the first cuvette portion 100, and the rest thereof (lower portion) is provided on the second cuvette portion 200. It has a top surface provided by part of the bottom surface of the first recess 110, a bottom surface provided by part of the bottom surface of the second recess 210, and side walls formed by side wall portions of the first recess 110 and side wall portions of the second recess 210, which are joined together. In this embodiment, the outlet passage 340 is U-shaped and includes a fourth passage section 304 and a straight fifth passage section 305. The fourth passage section 304 is a curved passage section, and an opening formed in its side wall on one side serves as the second passage port 320 from the cuvette cavity 300 to the outlet passage 340.

The fourth passage section 304 has an arc-shaped side wall portion away from the center of the cuvette cavity 300. The fifth passage section 305 is a straight passage section with a constant width, which is smoothly joined with the fourth passage section 304 at one end and is connected to the second through hole 122 at the other end. As shown in FIGS. 6, 7 and 8, the channel 226 for facilitating wetting of a liquid is provided on the second cuvette portion 200 in a side wall portion between the first passage port 310 and the second passage port 320 in the proximity of the second passage port 320. The channel 226 is an arc-shaped groove, which is provided in the bottom surface of the second recess 210, recessed toward the fourth recess 240 and is tangent to the side wall 227. It is provided in the cuvette cavity 300 in the bottom surface of the second recess 210. The first baffle sheet 125 and the second baffle sheet 225 projects within the outlet passage 340, forming the labyrinth-like structure. Preferably, the second baffle sheet 225 is disposed near the second passage port 320, whilst the first baffle sheet 125 is arranged at the curved fourth passage section 304.

In this embodiment, as shown in FIG. 2, the first through hole 121 and the second through hole 122 are both adjacent to one side wall of the first flange 150. The first through hole 121 is adjacent to a middle portion of the side wall, and the second through hole 122 is adjacent to an end portion of the side wall. Here, the term "adjacent" means neighboring or adjoining. Preferably, distances from the first through hole 121 and the second through hole 122 to the side wall are not greater than 5 mm. A distance from the first through hole 121 to a middle point of the side wall is not greater than 1 mm, a distance from the second through hole 122 to one end of the side wall is not greater than 5 mm.

In this embodiment, as shown in FIG. 6, the first passage port 310 and the second passage port 320 are disposed on opposite sides of a line 307 connecting the first through hole 121 and the center 306 of the cuvette cavity 300. In particular, the first passage port 310 and the second passage port 320 are respectively adjacent to (or situated at) two corners of the cuvette cavity 300 that are close to the first through hole 121, i.e., the third corner 357 and the fourth corner 358. As shown in FIG. 1, the first through hole 121 is shaped like a funnel and has a larger first opening 123 on the external surface of the first cuvette portion 100 and a smaller second opening 124 on the joining surfaces 1. It communicates with the inlet passage 330 through the smaller second opening 124. The second through hole 121 is cylindrical and has an opening on the external surface of the first cuvette portion 100 and another opening on the bottom surface of the first recess 110. It communicates with the outlet passage 340 through the opening on the bottom surface of the first recess 110. In this embodiment, a distance between the first through hole 121 and the second through hole 122 is not less than half a distance between the first passage port 310 and the second passage port 320, and an edge-to-edge distance between the openings of the two through holes on the external surface of the first cuvette portion 100 is not less than 2 mm.

Figure 9:
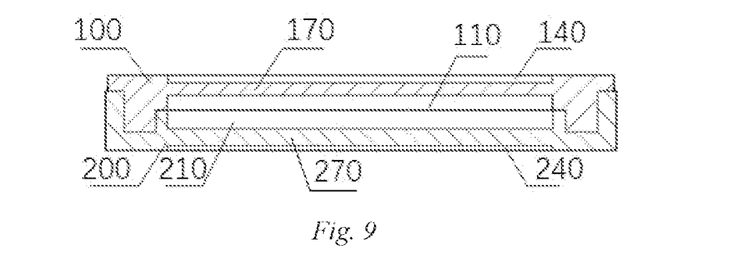
FIG. 9 is a schematic illustration of a first viewing window and a second viewing window.

Preferably, as shown in FIG. 9, when looking through the bottom surface of the third recess 140, the entire cuvette cavity 300 can be seen. Moreover, when looking through the bottom surface of the fourth recess 240, the entire cuvette cavity 300 can be seen. In this embodiment, a portion between the bottom surface of the third recess 140 and the bottom surface of the first recess 110 serves as a first viewing window 170 for the cuvette cavity 300, and a portion between the bottom surface of the fourth recess 240 and the bottom surface of the second recess 210 serves as a second viewing window 270 for the cuvette cavity 300. During use of the cuvette for analysis of liquids according to the present application, probing light propagates through both the first viewing window 170 and the second viewing window 270. The probing light passes through the first viewing window 170 and reaches an object on the bottom surface of the cuvette cavity 300, and part of it transmits through the second viewing window 270 and forms an image, for example, on an analysis lens of a microscope. Therefore, in order to achieve good optical analysis, the first viewing window 170 is preferred to be thinner.

As shown in FIG. 4, the cuvette for analysis of liquids according to the present application may be further provided with a calibration mark 260 for providing a reference, for example, for adjusting a focal length of the analysis lens in the microscope during optical analysis. The calibration mark 260 is provided on the bottom surface of the cuvette cavity 300, preferably under the bottom surface of the second recess 210 on the second cuvette portion 200. Conventionally, a concavo-convex pattern is formed by injection molding as such a calibration mark. As errors will be introduced during injection molding, the concavo-convex pattern formed by injection molding is associated with very low yield and therefore not able to serve as an effective calibration mark that can be readily recognized optically. In this embodiment, the calibration mark 260 is a photolithographic pattern formed by photolithography, which is more favorable to optical recognition. Moreover, accurate size control is allowed during fabrication, making it suitable for mass production at high yield. Preferably, the calibration mark 260 is formed photolithographically under the bottom surface of the cuvette cavity 300. It may be any pattern favorable to observation, for example, by an analysis lens of a microscope. In this embodiment, it is preferred to be a set of regular circles.

In order to fill a liquid to be analyzed into the cuvette for analysis of liquids of the present application, the cuvette is placed horizontally, with the first cuvette portion 100 overlying the second cuvette portion 200. A proper amount of the liquid to be analyzed is sucked into a pipette and injected from the larger first opening 123 of the first through hole 121. It then enters the inlet passage 330 from the first through hole 121, and sequentially passes through the third passage section 301, the second passage section 302 and the first passage section 303. After passing through the first passage port 310, the liquid spreads fanwise into the cuvette cavity 300. During the spreading, it preferentially wets the channel 226. After the cuvette cavity 300 is filled up, the liquid enters the outlet passage 340 from the second passage port 320. It first enters the fourth passage section 304, then passes through the second baffle plate 225 in the second cuvette portion 200 and the first baffle plate 125 in the first cuvette portion 100, and finally reaches the fifth passage section 305 and the second through hole 122. As a result, air that has been present in the inlet passage 330, the cuvette cavity 300 and the outlet passage 340 of the cuvette is expelled to leave the cuvette from the second through hole 122. At this point, optical analysis of the liquid to be analyzed can be carried out. Moreover, a centrifugal operation can also be performed if needed.

Preferred specific embodiments have been described in detail above. It is to be understood that, those of ordinary skill in the art, without the need for creative effort, can make various modifications and changes, based on the concept of the present invention. Accordingly, all the technical solutions that can be obtained by those skilled in the art by logical analysis, inference or limited experimentation in accordance with the concept of the invention on the basis of the prior art are intended to fall within the protection scope as defined by the claims.

The invention claimed is:
1. A cuvette for analysis of liquids, comprising:
a first cuvette portion and a second cuvette portion, which are joined together, with a cuvette cavity, an inlet passage and an outlet passage being formed between the first cuvette portion and the second cuvette portion, the inlet passage and the outlet passage both in communication with the cuvette cavity,
wherein the outlet passage is provided therein with a labyrinth-like sealing structure, which prevents backfill of a gas that has been discharged from the outlet passage during filling of a liquid to be analyzed in the cuvette.

2. The cuvette for analysis of liquids of claim 1, wherein the labyrinth-like sealing structure comprises at least two baffle blocks, each of which projects inwardly from an inner wall of the outlet passage and blocks part of a path within the outlet passage, and which are arranged in a sequentially staggered manner.

3. The cuvette for analysis of liquids of claim 2, wherein the at least two baffle blocks include a first baffle block and a second baffle block, which project inwardly from the inner walls of the outlet passage respectively in two opposite directions.

4. The cuvette for analysis of liquids of claim 1, wherein the cuvette cavity is provided therein with an elongate groove, which facilitates wetting of the liquid and is located at a bottom of the cuvette cavity and is adjacent to a side wall of the cuvette cavity.

5. The cuvette for analysis of liquids of claim 4, wherein the elongate groove is so formed as to be recessed from the bottom of the cuvette cavity and has a cross-section which is arc-shaped and tangent to the side wall that it is adjacent to.

6. The cuvette for analysis of liquids of claim 1, wherein the inlet passage is provided with a first passage port in communication with the cuvette cavity at one end and with a first through hole in communication with the outside of the cuvette at the other end, and the outlet passage is provided with a second passage port in communication with the cuvette cavity at one end and with a second through hole in communication with the outside of the cuvette at the other end.

7. The cuvette for analysis of liquids of claim 6, wherein the outlet passage has a U-like shape with one arm in communication with the cuvette cavity and another arm in communication with the second through hole.

8. The cuvette for analysis of liquids of claim 6, wherein the first passage port and the second passage port are located respectively on opposite sides of a line connecting the first through hole and a center of the cuvette cavity.

9. The cuvette for analysis of liquids of claim 6, wherein the inlet passage comprises a first passage section, which provides the first passage port at one end and has an inner diameter varying so as to be greater at a location of the first passage section closer to the first passage port.

10. The cuvette for analysis of liquids of claim 9, wherein the inlet passage further comprises a second passage section in communication with the first passage section and a third passage section in communication with the second passage section, the second passage section being straight and having a constant width, the third passage section curved and in communication with the second through hole at one end.

11. The cuvette for analysis of liquids of claim 6, wherein the first through hole resembles a funnel having a first opening formed at its larger end and a second opening formed at its smaller end, the first opening in communication with the outside of the cuvette, the second opening in communication with the inlet passage.

12. The cuvette for analysis of liquids of claim 1, wherein the cuvette further comprises a calibration mark disposed within the cuvette cavity on a bottom surface of the second cuvette portion.

13. The cuvette for analysis of liquids of claim 12, wherein the calibration mark is a photolithographic pattern formed by a photolithographic process.

14. The cuvette for analysis of liquids of claim 6, wherein the first cuvette portion is provided thereon with a first recess and the second cuvette portion is provided thereon with a second recess, the first recess open toward the second cuvette portion, the second recess open toward the first cuvette portion, the first recess and the second recess confining a space therebetween, which forms the cuvette cavity, the inlet passage and the outlet passage; the first through hole and the second through hole are both provided on the first cuvette portion.

15. The cuvette for analysis of liquids of claim 14, wherein the first cuvette portion is provided in an external surface thereof with a third recess and the second cuvette portion is provided in an external surface thereof with a fourth recess, the third recess and the fourth recess having bottom surfaces, which are both flat, smooth and parallel to joining surfaces of the first cuvette portion and the second cuvette portion; a portion of the first cuvette portion between a bottom surface of the third recess and a bottom surface of the first recess forms a first viewing window for the cuvette cavity, and a portion of the second cuvette portion between a bottom surface of the fourth recess and a bottom surface of the second recess forms a second viewing window for the cuvette cavity.

16. The cuvette for analysis of liquids of claim 1, wherein the cuvette cavity has two corners away from the outlet passage and the inlet passage, which are rounded.

17. The cuvette for analysis of liquids of claim 1, wherein the first cuvette portion and the second cuvette portion are injection-molded.

18. A cuvette for analysis of liquids, comprising:
a first cuvette portion and a second cuvette portion, which are joined to each other, the first cuvette portion having a first recess, a first through hole and a second through hole, the second cuvette portion having a second recess, the first recess recessed in a direction from an internal surface of the first cuvette portion to an external surface thereof, the first recess open toward the second cuvette portion, the second recess recessed in a direction from an internal surface of the second cuvette portion to an external surface thereof, the second recess open toward the first cuvette portion, the first recess and the second recess confining a space therebetween forming a cuvette cavity, an inlet passage and an outlet passage, which are in communication with one another, the first through hole extending through the first cuvette portion in a thickness direction of the first cuvette portion and coming into communication with the inlet passage, the second through hole extending through the first cuvette portion in the thickness direction of the first cuvette portion and coming into communication with the outlet passage,
a first passage port from the inlet passage to the cuvette cavity and a second passage port from the cuvette cavity to the outlet passage disposed respectively on opposite sides of a line connecting the first through hole to a center of the cuvette cavity, wherein a backflow edge of the cuvette cavity is provided thereat with an elongate groove, which is a groove disposed in a bottom surface of the second recess and extends along a lengthwise direction of a side wall of the cuvette cavity, the elongate groove having a cross-section, which is arc-shaped and tangent to a side wall of the second recess; and the outlet passage is provided therein with a first baffle block and a second baffle block, which project inwardly from inner walls of the outlet passage respectively in two opposite directions and block part of a path within the outlet passage, thereby forming a labyrinth-like sealing structure.

19. The cuvette for analysis of liquids of claim 18, wherein the cuvette further comprises a calibration mark, which is disposed within the cuvette cavity on a bottom surface of the second cuvette portion and is a photolithographic pattern formed by a photolithographic process.

20. The cuvette for analysis of liquids of claim 19, wherein the first cuvette portion and the second cuvette portion are both injection-molded and are joined together by welding.

* * * * *